(12) United States Patent
Bednarek

(10) Patent No.: US 7,314,861 B2
(45) Date of Patent: *Jan. 1, 2008

(54) MELANIN-CONCENTRATING HORMONE ANALOGS

(75) Inventor: Maria Bednarek, Colonia, NJ (US)

(73) Assignee: Merck & Co., Inc., Rahway, NJ (US)

( * ) Notice: Subject to any disclaimer, the term of this patent is extended or adjusted under 35 U.S.C. 154(b) by 469 days.

This patent is subject to a terminal disclaimer.

(21) Appl. No.: 10/477,985

(22) PCT Filed: May 28, 2002

(86) PCT No.: PCT/US02/16513

§ 371 (c)(1),
(2), (4) Date: Nov. 17, 2003

(87) PCT Pub. No.: WO02/097037

PCT Pub. Date: Dec. 5, 2002

(65) Prior Publication Data

US 2004/0147432 A1    Jul. 29, 2004

Related U.S. Application Data

(60) Provisional application No. 60/294,806, filed on May 31, 2001.

(51) Int. Cl.
*A61K 38/00* (2006.01)

(52) U.S. Cl. ......................................................... 514/9

(58) Field of Classification Search ...................... None
See application file for complete search history.

(56) References Cited

U.S. PATENT DOCUMENTS

| 5,049,655 A | 9/1991 | Vaughan et al. |
| 5,849,708 A | 12/1998 | Maratos-Flier |
| 2003/0105278 A1* | 6/2003 | Bednarek .................. 530/317 |

FOREIGN PATENT DOCUMENTS

| WO | WO 90/11295 | 10/1990 |
| WO | WO 07/57070 | 8/2001 |

OTHER PUBLICATIONS

Audinot, V. et al. "Structure-Activity Relationship Studies of Melanin-concentrating Hormone (Mcl-II-related Peptide Ligands at SLC-1, the Human MCH Receptor", The Journal of Biological Chemistry, 2001, vol. 276, pp. 13554-13562—applicant's submitted IDS.*
Audinot et al, Structure-activity relationship studies of melanin-concentrating hormone (MCH)-related peptide ligands at SLC-1, the human MCH receptor, J Biol Chem. Apr. 27, 2001; 276(17):13554-62.*
Hinterman E. et al, J. of Receptor and Signal Transduction Research, 19(1-4), 411-422, (1999).*
Audinot V, "Structure-activity relationship studies of melanin-concentrating hormone (MCH)-related peptide ligands at SLC-1, the human MCH receptor," J Biol Chem. Apr. 27, 2001;276(17):13554-62. Epub Jan. 18, 2001.*
Audinot, V. et al. "Structure-Activity Relationship Studies of Melanin-concentrating Hormone (MCH)-related Peptide Ligands at SLC-1, the Human MCH Receptor", The Journal of Biological Chemistry, 2001, vol. 276, pp. 13554-13562.
Bachner, D. et al. "Identification of melanin concentrating hormone (MCH) as the natural ligand for the orphan somatostatin-like receptor 1 (SLC-1)", FEBS Letters, 1999, vol. 457, pp. 522-524.
Baker, B. et al. "Structure-Activity Studies With Fragments and Analogues of Salmonid Melanin-Concentrating Hormone", Peptides, 1990, vol. 11, pp. 1103-1108.
Bednarek, M. et al. "Short Segment of Human Melanin-Concentrating Hormone That Is Sufficient for Full Activation of Human Melanin-Concentrating Hormone Receptors 1 and 2", Biochemistry, 2001, vol. 40, pp. 9379-9386.
Breton, C. et al. "Isolation and characterization of the human melanin-concentrating hormone gene and a variant gene", Mulecular Brain Research, 1993, vol. 18, pp. 297-310.
Chambers, J. et al. "Melanin-concentrating hormone is the cognate ligand for the orphan G-protein-coupled receptor SLC-1", Nature, 1999, vol. 400, pp. 261-265.
Chimania, M. et al. "Predominant GABAB Mediated Dispersion of the Isolated Web Melanophores of the Indian Bull Frog, Rana Tigerina (Daud.)", Indian Journal of Pharmacology, 1995, vol. 27, pp. 241-244.
Drozdz, R. et al. "(D-(p-Benzoylphenylalanine)13, Tyrosine19)-Melanin-concentrating Hormone, a Potent Analogue for MCH Receptor Crosslinking", Journal of Peptide Science, 1999, vol. 5, pp. 234-242.
Drozdz, R. et al. "Melanin-concentrating hormone binding to mouse melanoma cells in vitro", FEBS Letters, 1995, vol. 359, pp. 199-202.
Erickson, J. et al. "Sensitivity to leptin and susceptibility to seizures of mice lacking neuropeptide Y", Nature, 1996, vol. 381, pp. 415-418.
Flier, J. et al. "Obesity and the Hypothalamus: Novel Peptides for New Pathways", Cell, 1998, vol. 92, pp. 437-440.
Hintermann, E. et al. "Synthesis and Characterization of New Radioligands for the Mammalian Melanin-Concentrating Hormone (MCH) Receptor", Journal of Receptor & Signal Transduction Research, 1999, vol. 19, pp. 411-422.
Kawauchi, H. et al. "Characterization of melanin-concentrating hormone in chum salmon pituitaries", Nature, 1983, vol. 305, pp. 321-323.

(Continued)

*Primary Examiner*—Anish Gupta
*Assistant Examiner*—Thomas S. Heard
(74) *Attorney, Agent, or Firm*—Catherine D. Fitch; Sheldon O. Heber

(57) ABSTRACT

The present invention features truncated MCH analogs active at the melanin concentrating hormone type 2 receptor (MCH-2R) and uses of such analogs. Truncated MCH analogs described herein include those active at MCH-2R and MCH-1R, and those selectively active at MCH-2R. MCH-2R analogs have a variety of different uses including being used as a research tool and being used therapeutically.

20 Claims, No Drawings

OTHER PUBLICATIONS

Knigge, K. et al. "Melanotropic Peptides in the Mammalian Brain: The Melanin-Concentrating Hormone", Peptides, 1996, vol. 17, pp. 1063-1073.

Lebl, M. et al. "Melanin Concentrating Hormone Analogues: Contraction of the Cyclic Structure. I. Angonist Activity", Journal of Medicinal Chemistry, 1988, vol. 31, pp. 949-954.

MacDonald, D. et al. "Molecular Characterization of the Melanin-Concentrating Hormone/Receptor Complex: Identification of Critical Residues Involved in Binding and Activation", Molecular Pharmacology, 2000, vol. 58, pp. 217-225.

Nahon, J. "The Melanin-Concentrating Hormone: From the Peptide to the Gene", Critical Reviews in Neurobiology, 1994, vol. 8, pp. 221-262.

Presse, F. et al. "Structure of the Human Melanin Concentrating Hormone mRNA", Molecular Endocrinology, 1990, vol. 4, pp. 632-637.

Qu, D. et al. "A role for melanin-concentrating hormone in the central regulation of feeding behaviour", Nature, 1996, vol. 380, pp. 243-247.

Saito, Y. et al. "Molecular characterization of the melanin-concentrating-hormone receptor", Nature, 1999, vol. 400, pp. 265-269.

Shimada, M. et al. "Mice lacking melanin-concentrating hormone are hypophagic and lean", Nature, 1998, vol. 396, pp. 670-674.

Shimomura, Y. et al. "Isolation and Identification of Melanin-Concentrating Hormone as the Endogenous Ligand of the SLC-1 Receptor", Biochemical and Biophysical Research Communications, 1999, vol. 261, pp. 622-626.

Vaughan, J. et al. "Characterization of Melanin-Concentrating Hormone from Rat Hypothalamus", Endocrinology, 1989, vol. 125, pp. 1660-1665.

* cited by examiner

MELANIN-CONCENTRATING HORMONE ANALOGS

CROSS-REFERENCE TO RELATED APPLICATIONS

The present application claims priority to provisional application U.S. Ser. No. 60/294,806, filed May 31, 2001, hereby incorporated by reference herein.

BACKGROUND OF THE INVENTION

The references cited in the present application are not admitted to be prior art to the claimed invention.

Neuropeptides present in the hypothalamus play a major role in mediating the control of body weight. (Flier, et al., 1998. *Cell*, 92, 437-440.) Melanin-concentrating hormone (MCH) is a cyclic 19-amino acid neuropeptide synthesized as part of a larger pre-prohormone precursor in the hypothalamus which also encodes neuropeptides NEI and NGE. (Nahon, et al., 1990. *Mol. Endocrinol.* 4, 632-637.) MCH was first identified in salmon pituitary, and in fish MCH affects melanin aggregation thus affecting skin pigmentation. In trout and in eels MCH has also been shown to be involved in stress induced or CRF-stimulated ACTH release (Kawauchi, et al., 1983. *Nature* 305, 321-323.)

In humans two genes encoding MCH have been identified that are expressed in the brain. (Breton, et al., 1993. *Mol. Brain Res.* 18, 297-310.) In mammals MCH has been localized primarily to neuronal cell bodies of the hypothalamus which are implicated in the control of food intake, including perikarya of the lateral hypothalamus and zona inertia. (Knigge, et al., 1996. *Peptides* 17, 1063-1073.)

Pharmacological and genetic evidence suggest that the primary mode of MCH action is to promote feeding (orexigenic). MCH mRNA is up regulated in fasted mice and rats, in the ob/ob mouse and in mice with targeted disruption in the gene for neuropeptide Y (NPY). (Qu, et al., 1996. *Nature* 380, 243-247, Erickson, et al., 1996. *Nature* 381, 415-418.) Injection of MCH centrally (ICV) stimulates food intake and MCH antagonizes the hypophagic effects seen with α melanocyte stimulating hormone (αMSH). (Qu, et al., 1996. *Nature* 380, 243-247.) MCH deficient mice are lean, hypophagic and have increased metabolic rate. (Shimada, et al., 1998. *Nature* 396, 670-673.)

MCH action is not limited to modulation of food intake as effects on the hypothalamic-pituitary-axis have been reported. (Nahon, 1994. *Critical Rev. in Neurobiol.* 8, 221-262.) MCH can modulate stress-induced release of ACTH in mammals. (Nahon, 1994. *Critical Rev. in Neurobiol* 8, 221-262.)

Several references describe a receptor that is indicated to bind MCH ("MCH-1R"). (Chambers, et al., 1999. *Nature* 400, 261-265, Saito, et al., 1999. *Nature* 400, 265-269, Bächner, et al., 1999. *FEBS Letters* 457:522-524, Shimomura, et al., 1999. *Biochemical and Biophysical Research Communications* 261, 622-626.)

SUMMARY OF THE INVENTION

The present invention features truncated MCH analogs active at the melanin concentrating hormone type 2 receptor ("MCH-2R"). Truncated MCH analogs include compounds active at MCH-2R and MCH-1R, and those selectively active at MCH-2R. Truncated MCH analogs have a variety of uses including being used as a research tool and being used therapeutically.

Truncated MCH analogs selective for MCH-2R exert a greater activity at MCH-2R than at MCH-1R. MCH activities at MCH-R1 and MCH-R2 include receptor binding and receptor activation. Truncated analogs selectively active at MCH-2R can have an increased binding, an increased activity, or both an increased binding and an increased activity at MCH-2R. Preferably, the difference between the levels of activity at MCH-2R and MCH-1R is at least about two-fold or at least about three-fold.

Receptor activation, or the ability to activate MCH-2R, indicates that the analog is able to produce MCH-2R functional activity for at least one of the human, ferret, dog, or rhesus monkey MCH-2R under at least in vitro conditions. Techniques for measuring in vitro functional activity of MCH-2R include measuring G-protein activity. MCH analogs functionally active in vitro are expected to have some activity in vivo.

Truncated MCH analogs have the structure:

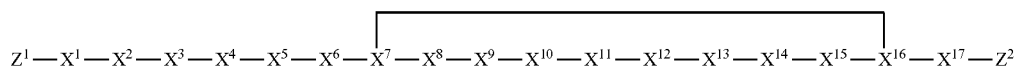

wherein $X^1$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof;

$X^2$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof;

$X^3$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid or glutamic acid, or a derivative thereof;

$X^4$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, glutamic acid, or a derivative thereof, $X^5$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid or glutamic acid, or a derivative thereof;

$X^6$ is an optionally present amino acid that, if present, is either arginine or des-amino-arginine;

$X^7$ is cysteine;

$X^8$ is either methionine, alanine, or norleucine;

$X^9$ is either leucine or alanine;

$X^{10}$ is either glycine, alanine, leucine, norleucine, serine, sarcosine, isobutyric acid, gamma-aminobutyric acid, D-leucine, D-alanine, D-norleucine, D-asparagine, D-serine, β-alanine, phenylglycine, 2-cyclohexyl-alanine, or D-phenylalanine;

$X^{11}$ is either arginine, alanine, N-methyl-arginine, homoarginine, citrulline, norleucine, or nitroarginine;

$X^{12}$ is either valine or alanine;

$X^{13}$ is either phenylalanine, tyrosine, D-(p-benzoylphenylalanine), (1')- and (2')-naphthylalanine, cyclohexylalanine, or mono and multi-substituted phenylalanine wherein each substituent is independently selected from the group consisting of O-alkyl, alkyl, OH, $NO_2$, $NH_2$, F, I, and Br;

$X^{14}$ is arginine;

$X^{15}$ is alanine, proline or sarcosine;

$X^{16}$ is either cysteine or D-cysteine;

$X^{17}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid or glutamic acid, or a derivative thereof;

$Z^1$ is an optionally present protecting group that, if present, is covalently joined to the N-terminal amino group;

$Z^2$ is an optionally present protecting group that, if present, is covalently joined to the C-terminal carboxy group;

or a labeled derivative of said peptide;

or a pharmaceutically acceptable salt of said peptide or of said labeled derivative.

Unless otherwise stated, those amino acids with a chiral center are provided in the L-enantiomer. Reference to "a derivative thereof" refers to the corresponding D-amino acid, N-alkyl-amino acid, β-amino acid, and ω-amino acid.

Truncated MCH analogs selectively active at MCH-2R can be produced by, for example, modifying $X^6$, $X^8$, $X^{10}$ or $X^{11}$. Examples of modifications providing for selective MCH-2R activity include one or more of the following: $X^6$ is des-amino-arginine; $X^8$ is alanine; $X^{10}$ is either isobutyric acid, D-alanine, D-leucine, D-asparagine, D-norleucine, D-serine, β-alanine, phenylglycine, 2-cyclohexyl-alanine, or D-phenylalanine; and $X^{11}$ is alanine, nitroarginine, citrulline, norleucine, or homoarginine.

Thus, a first aspect of the present invention describes a truncated MCH analog wherein at least one of $X^6$, $X^8$, $X^{10}$, and $X^{11}$ is selected from the group consisting of: $X^6$ is des-amino-arginine; $X^8$ is alanine; $X^{10}$ is either isobutyric acid, D-alanine, D-leucine, D-asparagine, D-norleucine, D-serine, β-alanine, phenylglycine, 2-cyclohexyl-alanine, or D-phenylalanine; and $X^{11}$ is alanine, nitroarginine, citrulline norleucine, or homoarginine.

Another aspect of the present invention describes a method of screening for a compound able to bind MCH-2R. The method comprises the step of measuring the ability of the compound to affect binding of a truncated MCH analog to MCH-2R.

Another aspect of the present invention describes a method of screening for a MCH-2R antagonist. The method involves activating a recombinantly produced MCH-2R receptor with a MCH-2R analog that activates MCH-2R, and measuring the ability of a compound to inhibit MCH-2R activity.

Another aspect of the present invention describes a method of selectively activating MCH-2R and measuring the effect of a test compound on MCH-2R activity. The method comprises the steps of (a) contacting MCH-2R or a functional derivative thereof with a compound that selectively activates MCH-2R and a test compound; and (b) measuring MCH-2R activity.

Another aspect of the present invention describes a method for increasing weight in a subject. The method comprises the step of administering to the subject an effective amount of a truncated MCH analog that activates MCH-2R to produce a weight increase.

Another aspect of the present invention describes a method for increasing appetite in a subject. The method comprises the step of administering to the subject an effective amount of a truncated MCH analog that activates MCH-2R to produce an appetite increase.

Another aspect of the present invention describes a method for measuring the ability of a compound to decrease weight or appetite in a subject. The method involves administering to the subject an effective amount of a truncated MCH analog that would produce a weight or appetite increase and measuring the effect of the compound on weight or appetite.

Other features and advantages of the present invention are apparent from the additional descriptions provided herein including the different examples. The provided examples illustrate different components and methodology useful in practicing the present invention. The examples do not limit the claimed invention. Based on the present disclosure the skilled artisan can identify and employ other components and methodology useful for practicing the present invention.

DETAILED DESCRIPTION OF THE INVENTION

MCH analogs described herein contain about 10 to about 17 amino acids or amino acid derivatives and are active at MCH-2R. Using the present application as a guide MCH analogs can be produced having significant MCH-R2 receptor activity, and in some cases having activity equal to or better than naturally occurring mammalian MCH. The smaller size of truncated MCH analogs offers advantages over full-length MCH such as ease of synthesis and/or increased solubility in physiological buffers.

Significant activity at MCH-2R is activity that is at least about 50%, at least about 75%, or at least about 100% of activity compared to the activity obtained using human MCH. MCH-2R activity can be assayed using techniques measuring G-protein activity such as those described in the Example provided below.

Uses of truncated MCH analogs include research tool and therapeutic applications. Research tool applications generally involve the use of a truncated MCH analog and MCH-2R. MCH-2R can be present in different environments such as a mammalian subject, a whole cell, and membrane fragments. Examples of research tool applications of truncated MCH analogs include screening for compounds active at MCH-2R, determining whether MCH-2R may be present in a sample or preparation, examining the role or effect of MCH and MCH-2R activation, and examining the role or effect of MCH antagonists.

Truncated MCH analogs selectivity active at MCH-2R have additional uses related to the selective activity. Examples of additional uses include being used to explore differences between MCH-1R and MCH-2R and to distinguish between the presence of MCH-1R and MCH-2R.

Truncated MCH analogs can be used to screen for both MCH agonists and MCH antagonists. Screening for MCH agonists can be performed, for example, by using a truncated MCH analog in a competition experiment with test compounds. Screening for MCH antagonists can be performed, for example, by using a truncated MCH analog to produce MCH-2R activity and then measuring the ability of a test compound to alter such activity.

Therapeutic applications of truncated MCH analogs involve administration to a subject containing an MCH-2R. Subjects possessing MCH-2R include humans, dogs, ferrets, and rhesus monkeys.

Reference to subject does not necessarily indicate the presence of a disease or disorder. The term subject includes, for example, humans being treated to help alleviate a disease or disorder, and humans being treated prophylactically to retard or prevent the onset of a disease or disorder.

MCH agonists can be used to achieve a beneficial effect in a subject. For example, a MCH agonist can be used to facilitate a weight gain, maintenance of weight and/or an appetite increase. Such effects are particularly useful for a patient having a disease or disorder, or under going a treatment, accompanied by weight loss. Examples of diseases or disorders accompanied by weight loss include anorexia, AIDS, wasting, cachexia, and frail elderly. Examples of treatments accompanied by weight loss include chemotherapy, radiation therapy, and dialysis.

MCH antagonists can also be used to achieve a beneficial effect in a patient. For example, a MCH antagonist can be used to facilitate weight loss, appetite decrease, weight maintenance, cancer (e.g., colon or breast) treatment, pain reduction, stress reduction and/or treatment of sexual dysfunction.

Truncated MCH-2R Active Analogs

A truncated MCH-2R active analog is an optionally modified peptide having the structure:

or tyrosine; more preferably, $X^2$ if present is phenylalanine; and more preferably, $X^2$ is not present;

$X^3$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid or glutamic acid, or a derivative thereof; preferably, $X^3$ if present is aspartic acid or glutamic acid; more preferably, $X^3$ if present is aspartic acid; and more preferably, $X^3$ is not present;

$X^4$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, glutamic acid, or a derivative thereof; preferably, $X^4$ if present is methionine, leucine, isoleucine, valine, or alanine; more preferably, $X^4$ if present is methionine; and more preferably, $X^4$ is not present;

$X^5$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid or glutamic acid, or a derivative thereof; preferably, $X^5$ if present is leucine, methionine, isoleucine, valine or alanine; more preferably, $X^5$ if present is leucine; and more preferably, $X^5$ is not present;

$X^6$ is an optionally present amino acid that, if present, is either arginine or des-amino-arginine; preferably, $X^6$ is arginine;

$X^7$ is cysteine;

$X^8$ is either methionine, alanine, or norleucine; preferably $X^8$ is methionine;

$X^9$ is either leucine or alanine; preferably, $X^9$ is alanine;

$X^{10}$ is either glycine, alanine, leucine, norleucine, serine, sarcosine, isobutyric acid, gamma-aminobutyric acid, D-leucine, D-alanine, D-norleucine, D-asparagine, D-serine, β-alanine, phenylglycine, 2-cyclohexyl-alanine, or D-phenylalanine; preferably, $X^{10}$ is either isobutyric acid, D-alanine, D-leucine, D-asparagine, D-norleucine, D-serine, β-alanine, phenylglycine, 2-cyclohexyl-alanine, or D-phenylalanine; more preferably, $X^{10}$ is either isobutyric acid, D-alanine, D-leucine, D-serine or D-asparagine;

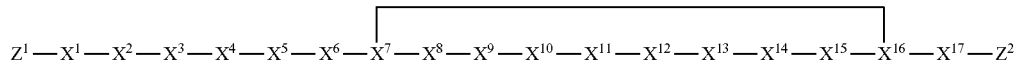

wherein $X^1$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^1$ if present is aspartic acid or glutamic acid; more preferably, $X^1$ if present is aspartic acid; and more preferably, $X^1$ is not present;

$X^2$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid, or glutamic acid, or a derivative thereof; preferably, $X^2$ if present is phenylalanine $X^{11}$ is either arginine, alanine, N-methyl-arginine, citrulline, homoarginine, nitroarginine or norleucine; preferably, $X^{11}$ is alanine, nitroarginine or norleucine;

$X^{12}$ is valine or alanine, preferably $X^{12}$ is valine;

$X^{13}$ is either phenylalanine, tyrosine, D-(p-benzoylphenylalanine), (1')- and (2')-naphthylalanine, cyclohexylalanine, or mono and multi-substituted phenylalanine wherein each substituent is independently selected from the group consisting of O-alkyl, alkyl, OH, $NO_2$, $NH_2$, F, I, and Br; preferably, $X^{13}$ is either phenylalanine, (2')napthylalanine, p-fluoro-phenylalanine, or cyclohexylalanine;

$X^{14}$ is arginine;

$X^{15}$ is alanine, proline or sarcosine, preferably, $X^{15}$ is proline or sarcosine;

$X^{16}$ is either cysteine or D-cysteine;

$X^{17}$ is an optionally present amino acid that, if present, is either alanine, valine, leucine, isoleucine, proline, tryptophan, phenylalanine, methionine, glycine, serine, threonine, tyrosine, cysteine, asparagine, glutamine, lysine, arginine, histidine, aspartic acid or glutamic acid, or a derivative thereof; preferably, $X^{17}$ if present is tyrosine or tryptophan; more preferably $X^{17}$ is not present;

$Z^1$ is an optionally present protecting group that, if present, is covalently joined to the N-terminal amino group;

$Z^2$ is an optionally present protecting group that, if present, is covalently joined to the C-terminal carboxy group;

or a labeled derivative of said peptide;

or a pharmaceutically acceptable salt of said peptide or of said labeled derivative.

The present invention comprehends diastereomers as well as their racemic and resolved enantiomerically pure forms. Truncated MCH analogs can contain D-amino acids, L-amino acids, or a combination thereof.

In different embodiments, MCH analogs contain a preferred (or more preferred) group at one or more different locations. More preferred embodiments contain preferred (or more preferred) groups in more of the different locations.

A protecting group covalently joined to the N-terminal amino group reduces the reactivity of the amino terminus under in vivo conditions. Amino protecting groups include optionally substituted —$C_{1-10}$ alkyl, optionally substituted —$C_{2-10}$ alkenyl, optionally substituted aryl, —$C_{1-6}$ alkyl optionally substituted aryl, —C(O)—$(CH_2)_{1-6}$—COOH, —C(O)—$C_{1-6}$ alkyl, —C(O)-optionally substituted aryl, —C(O)—O—$C_{1-6}$ alkyl, and —C(O)—O-optionally substituted aryl. Preferably, the amino terminus protecting group is acetyl, propyl, succinyl, benzyl, benzyloxycarbonyl or t-butyloxycarbonyl.

A protecting group covalently joined to the C-terminal carboxy group reduces the reactivity of the carboxy terminus under in vivo conditions. The carboxy terminus protecting group is preferably attached to the α-carbonyl group of the last amino acid. Carboxy terminus protecting groups include amide, methylamide, and ethylamide.

"Alkyl" refers to an optionally substituted hydrocarbon, or optionally substituted hydrocarbon group joined by carbon-carbon single bonds. The alkyl hydrocarbon group may be straight-chain or contain one or more branches or cyclic groups. Preferably, the alkyl group is 1 to 4 carbons in length. Examples of alkyl include methyl, ethyl, propyl, isopropyl, cyclopropyl, butyl, and t-butyl. Alkyl groups may be substituted with one or more substituents selected from the group consisting of halogen (preferably —F or —Cl), —OH, —CN, —SH, —$NH_2$, —$NO_2$, —$C_{1-2}$ alkyl substituted with 1 to 6 halogens (preferably —F or —Cl, more preferably —F), —$CF_3$, —$OCH_3$, or —$OCF_3$. In different embodiments the alkyl has none or one substituent.

"Alkenyl" refers to an optionally substituted hydrocarbon group containing one or more carbon-carbon double bonds. The alkenyl hydrocarbon group may be straight-chain or contain one or more branches or cyclic groups. Preferably, the alkenyl group is 2 to 4 carbons in length. Alkenyl groups may be substituted with one or more substituents selected from the group consisting of halogen (preferably —F or —Cl), —OH, —CN, —SH, —$NH_2$, —$NO_2$, —$C_{1-2}$ alkyl substituted with 1 to 5 halogens (preferably —F or —Cl, more preferably —F), —$CF_3$, —$OCH_3$, or —$OCF_3$. In different embodiments the alkenyl has none or one substituent.

"Aryl" refers to an optionally substituted aromatic group with at least one ring having a conjugated pi-electron system, containing up to two conjugated or fused ring systems. Aryl includes carbocyclic aryl, heterocyclic aryl and biaryl groups. Preferably, the aryl is a 5 or 6 membered ring, more preferably benzyl. Aryl groups may be substituted with one or more substituents selected from the group consisting of —$C_{1-4}$ alkyl, —$C_{1-4}$ alkoxy, halogen (preferably —F or —Cl), —OH, —CN, —SH, —$NH_2$, —$NO_2$, —$C_{1-2}$ alkyl substituted with 1 to 5 halogens (preferably —F or —Cl, more preferably —F), —$CF_3$, or —$OCF_3$. In different embodiments the aryl group has three, two, one, or zero, substituents.

A labeled derivative indicates the presence of a detectable label. Examples of detectable labels include luminescent, enzymatic, and radioactive labels. A preferred radiolabel is $^{125}I$. Both the type of label and the position of the label can affect MCH activity. Labels should be selected so as not to substantially alter the activity of the truncated MCH analog at MCH-2R. The effect of a particular label on MCH activity can be determined using assays measuring MCH activity and/or binding.

In preferred embodiments the optionally modified peptide has the structure:

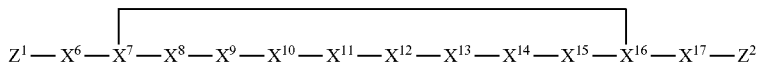

wherein the different groups, and preferred groups, are as described above. Preferred embodiments can be produced having different combinations and numbers of preferred and/or more preferred groups.

Truncated MCH Analogs Selective for MCH-2R

Truncated MCH analogs selective for MCH-2R can be produced, for example, having the structure of a truncated MCH analog where one or more of the following groups are present: $X^6$ is des-amino-arginine; $X^8$ is alanine; $X^{10}$ is either isobutyric acid, D-alanine, D-leucine, D-asparagine, D-norleucine, D-serine, β-alanine, phenylglycine, 2-cyclohexyl-alanine, or D-phenylalanine; and/or $X^{11}$ is alanine, nitroarginine, citrulline, norleucine, or homoarginine. More preferred groups provide for both increased binding and increased function activity. Examples of more preferred groups are $X^{10}$ being either isobutyric acid, D-norleucine, D-alanine, D-leucine D-asparagine, or D-serine.

In preferred embodiments concerning MCH-2R selectively active truncated analogs, the selectively active analog has the structure:

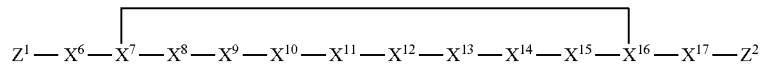

10 wherein the different groups, and preferred groups, are as described above for truncated MCH analogs, provided that one or more of the following groups are present: $X^6$ is des-amino-arginine; $X^8$ is alanine; $X^{10}$ is either isobutyric acid, D-alanine, D-leucine, D-asparagine, D-norleucine, D-serine, β-alanine, phenylglycine, 2-cyclohexyl-alanine, or D-phenylalanine; and $X^{11}$ is alanine, nitroarginine, citrulline, norleucine, or homoarginine. More preferred embodiments can be produced having different combinations and numbers of preferred and/or more preferred groups.

Specific examples of selectively active analogs are provided by SEQ. ID. NOs. 4, 11, 12, 13, 14, 15, 16, 17, 18, 19, 20, 23, 25, 26, 34, 35, 36, and 40. More preferred selectively active analogs are provided by SEQ. ID. NOs. 11, 13, 14, 18, 19, 35 and 36.

Production of Truncated MCH Analogs

Truncated MCH analogs can be produced using techniques well known in the art. For example, a polypeptide region of a truncated MCH analog can be chemically or biochemically synthesized and, if desired, modified to produce a blocked N-terminus and/or blocked C-terminus. Techniques for chemical synthesis of polypeptides are well known in the art. (See e.g., Vincent, in *Peptide and Protein Drug Delivery*, New York, N.Y., Dekker, 1990.) Examples of techniques for biochemical synthesis involving the introduction of a nucleic acid into a cell and expression of nucleic acids are provided in Ausubel, *Current Protocols in Molecular Biology*, John Wiley, 1987-1998, and Sambrook, et al., in *Molecular Cloning, A Laboratory Manual*, $2^{nd}$ Edition, Cold Spring Harbor Laboratory Press, 1989.

MCH-2R

MCH-2R is a G-protein coupled receptor that responds to MCH and is distinct from MCH-1R. Functional MCH-2R activity can be produced from naturally occurring human MCH-2R and functional derivatives thereof. Naturally occurring MCH-2R and functional derivatives thereof are activated by human MCH and are identified by the presence of at least 12 contiguous amino acids as that present in human MCH-2R. Reference to at least 12 contiguous amino acid provides a tag for the MCH-2R.

The amino acid sequence of the human MCH-2R receptor is provided for by SEQ. ID. NO. 58. MCH-2R functional derivatives contain a region with at least 12 contiguous amino acid from SEQ. ID. NO. 58 and are activated by MCH binding. In different embodiments, functional derivatives comprise at least about 30 consecutive amino acids present in SEQ. ID. NO. 58, or comprise or consist of SEQ. ID. NO. 58. Examples of functional derivatives of human MCH-2R include MCH-2R found in nature such as in the ferret, dog, or rhesus monkey and non-naturally occurring derivatives.

MCH-2R derivatives can be produced, for example, by starting with human MCH-2R. The amino acid and encoding cDNA sequences for MCH-2R are provided by SEQ. ID. NOs. 58 and 59. Functional derivatives of MCH-2R can be produced, for example, by introducing amino acid substitutions, additions and deletions.

Changes to MCH-2R to produce a derivative having essentially the same properties should be made outside of the MCH binding domain and in a manner not altering the tertiary structure. The ability of a polypeptide to have MCH-2R activity can be confirmed using techniques such as those measuring G-protein activity.

Differences in naturally occurring amino acids are due to different R groups. An R group affects different properties of the amino acid such as physical size, charge, and hydrophobicity. Amino acids can be divided into different groups as follows: neutral and hydrophobic (alanine, valine, leucine, isoleucine, proline, tyrptophan, phenylalanine, and methionine); neutral and polar (glycine, serine, threonine, tryosine, cysteine, asparagine, and glutamine); basic (lysine, arginine, and histidine); and acidic (aspartic acid and glutamic acid).

Generally, in substituting different amino acids it is preferable to exchange amino acids having similar properties. Substituting different amino acids within a particular group, such as substituting valine for leucine, arginine for lysine, and asparagine for glutamine are good candidates for not causing a change in polypeptide functioning.

Changes outside of different amino acid groups can also be made. Preferably, such changes are made taking into account the position of the amino acid to be substituted in the polypeptide. For example, arginine can substitute more freely for nonpolor amino acids in the interior of a polypeptide then glutamate because of its long aliphatic side chain. (See, Ausubel, *Current Protocols in Molecular Biology*, John Wiley, 1987-1998, Supplement 33 Appendix 1C.)

MCH Receptor Binding Assay

Assays measuring the ability of a compound to bind to MCH-2R employ a MCH-2R polypeptide comprising a MCH binding site. MCH-2R polypeptides include full-length human MCH-2R and functional derivatives thereof, truncated MCH-2R fragments containing the MCH binding site, and chimeric polypeptides comprising such MCH-2R fragments. A chimeric polypeptide comprising a MCH-2R fragment that binds MCH also contains one or more polypeptide regions not found in a naturally occurring MCH-2R. Preferably, assays measuring MCH binding employ full length MCH-2R of SEQ. ID. NO. 58.

The MCH-2R amino acid sequence involved in MCH binding can be identified using labeled MCH or truncated MCH analogs and different receptor fragments. Different strategies can be employed to select fragments to be tested to narrow down the binding region. Examples of such strategies include testing consecutive fragments about 15 amino acids in length starting at the N-terminus, and testing longer length fragments. If longer length fragments are tested, a fragment binding MCH can be subdivided or mutated to further locate the MCH binding region. Fragments used for binding studies can be generated using recombinant nucleic acid techniques.

Binding assays can be performed using individual compounds or preparations containing different numbers of compounds. A preparation containing different numbers of compounds having the ability to bind to the MCH-2R can be divided into smaller groups of compounds that can be tested to identify the compound(s) binding to the receptor. In an embodiment of the present invention a test preparation containing at least 10 compounds is used in a binding assay.

Binding assays can be performed using recombinantly produced MCH-2R polypeptides present in different environments. Such environments include, for example, cell extracts and purified cell extracts containing a MCH-2R polypeptide expressed from recombinant nucleic acid or naturally occurring nucleic acid; and also include, for example, the use of a purified MCH-2R produced by recombinant means or from naturally occurring nucleic acid which is introduced into a different environment.

Screening for MCH-2R Active Compounds

Screening for MCH-2R active compounds is facilitated using recombinant nucleic acid expressing a polypeptide having MCH-2R activity. Recombinantly expressed receptors offers several advantages in screening for receptor active compounds, such as the ability to express the receptor in a defined cell system so that responsiveness to receptor active compounds can more readily be differentiated from responses to other receptors. For example, MCH-2R can be expressed in a cell line such as HEK 293, COS 7, and CHO using an expression vector, wherein the same cell line without the expression vector can act as a control.

A recombinant "nucleic acid" refers to an artificial combination of two nucleotide sequence regions. The artificial combination is not found in nature. Recombinant nucleic acid includes nucleic acid having a first coding region and a regulatory element or a second coding region not naturally associated with the first coding region. Preferred recombinant nucleotide sequences are those where a coding region is under the control of an exogenous promoter, and where a second coding region is a selectable marker. The recombinant nucleotide sequence can be present in a cellular genome or can be part of an expression vector.

Preferably, expression is achieved in a host cell using an expression vector. An expression vector contains recombinant nucleic acid encoding a polypeptide along with regulatory elements for proper transcription and processing. The regulatory elements that may be present include those naturally associated with the recombinant nucleic acid and exogenous regulatory elements not naturally associated with the recombinant nucleic acid. Exogenous regulatory elements such as an exogenous promoter can be useful for expressing recombinant nucleic acid in a particular host.

Screening for MCH-2R active compounds is facilitated through the use of a truncated MCH analog in the assay. The truncated MCH analog provides for MCH-2R activity. The effect of test compounds on such activity can be measured to identify, for example, allosteric modulators and antagonists. Additionally, such assays can be used to identify agonists.

MCH Receptor Activity

MCH-1R and MCH-2R are G protein coupled receptors. MCH-1R couples to both Gi and Gq, while MCH-2R couples to Gq. Coupling of Gi results in the inhibition of adenylate cyclase and subsequent reductions in cAMP levels. Coupling to Gq leads to activation of phospholipase C and subsequent elevation of intracellular $Ca^{2+}$.

Techniques for measuring different G-protein activities, such as Gi, Gs, and Gq are well known in the art. Gi and Gs activity can be measured using techniques such as a melonaphore assay, assays measuring cAMP production, assays measuring inhibition of cAMP accumulation, and assays measuring binding of $^{35}S$-GTP. cAMP can be measured using different techniques such as a radioimmunoassay and indirectly by cAMP responsive gene reporter proteins.

Gq activity can be measured using techniques such as those measuring intracellular $Ca^{2+}$. Examples of techniques well known in the art that can be employed to measure $Ca^{2+}$ include the use of dyes such as Fura-2 and the use of $Ca^{2+}$-bioluminescent sensitive reporter proteins such as aequorin. An example of a cell line employing aequorin to measure G-protein activity is HEK293/aeq17. (Button, et al, 1993. *Cell Calcium* 14, 663-671, and Feighner, et al., 1999. *Science* 284, 2184-2188, both of which are hereby incorporated by reference herein.)

Chimeric receptors containing a MCH binding region functionally coupled to a G protein can also be used to measure MCH receptor activity. A chimeric MCH receptor contains an N-terminal extracellular domain; a transmembrane domain made up of transmembrane regions, extracellular loop regions, and intracellular loop regions; and an intracellular carboxy terminus. Techniques for producing chimeric receptors and measuring G protein coupled responses are provided for in, for example, International Application Number WO 97/05252, and U.S. Pat. No. 5,264,565.

Weight or Appetite Alteration

Truncated MCH analogs can be used in methods to increase or maintain weight and/or appetite in a subject. Such methods can be used, for example, as part of an experimental protocol examining the effects of MCH antagonists, to achieve a beneficial effect in a subject or to further examine the physiological effects of MCH.

Experimental protocols examining the effects of MCH antagonists can be performed, for example, by using a sufficient amount of a truncated MCH analog to produce a weight or appetite increase in a subject and then examining the effect of a test compound. Changes in weight and appetite can be measured using techniques well known in the art.

Increasing weight or appetite can be useful for maintaining weight or producing a weight or appetite gain in an under weight subject, or in a patient having a disease or undergoing treatment that affects weight or appetite. In addition, for example, farm animals possessing MCH-2R can be treated to gain weight.

Under weight subjects include those having a body weight about 10% or less, 20% or less, or 30% or less, than the lower end of a "normal" weight range or Body Mass Index ("BMI"). "Normal" weight ranges are well known in the art and take into account factors such as a patient age, height, and body type.

BMI measures your height/weight ratio. It is determined by calculating weight in kilograms divided by the square of height in meters. The BMI "normal" range is 19-22.

Administration

Truncated MCH analogs can be formulated and administered to a subject using the guidance provided herein along with techniques well known in the art. The preferred route of administration ensures that an effective amount of compound reaches the target. Guidelines for pharmaceutical administration in general are provided in, for example, *Remington's Pharmaceutical Sciences* 18$^{th}$ Edition, Ed. Gennaro, Mack Publishing, 1990, and *Modern Pharmaceutics* 2$^{nd}$ Edition, Eds. Banker and Rhodes, Marcel Dekker, Inc., 1990, both of which are hereby incorporated by reference herein.

Truncated MCH analogs can be prepared as acidic or basic salts. Pharmaceutically acceptable salts (in the form of water- or oil-soluble or dispersible products) include conventional non-toxic salts or the quaternary ammonium salts that are formed, e.g., from inorganic or organic acids or bases. Examples of such salts include acid addition salts such as acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, oxalate, pamoate, pectinate, persulfate, 3-phenylpropionate, picrate, pivalate, propionate, succinate, tartrate, thiocyanate, tosylate, and undecanoate; and base salts such as ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine and lysine.

Truncated MCH analogs can be administered using different routes such as by injection. When administered by injection, the injectable solution or suspension may be formulated using suitable non-toxic, parenterally-acceptable diluents or solvents, such as Ringer's solution or isotonic sodium chloride solution, or suitable dispersing or wetting and suspending agents, such as sterile, bland, fixed oils, including synthetic mono- or diglycerides, and fatty acids, including oleic acid.

Suitable dosing regimens are preferably determined taking into account factors well known in the art including type of subject being dosed; age, weight, sex and medical condition of the subject; the route of administration; the renal and hepatic function of the subject; the desired effect; and the particular compound employed.

Optimal precision in achieving concentrations of drug within the range that yields efficacy without toxicity requires a regimen based on the kinetics of the drug's availability to target sites. This involves a consideration of the distribution, equilibrium, and elimination of a drug. The daily dose for a subject is expected to be between 0.01 and 1,000 mg per subject per day.

Truncated MCH analogs can be provided in kit. Such a kit typically contains an active compound in dosage forms for administration. A dosage form contains a sufficient amount of active compound such that a weight or appetite increase can be obtained when administered to a subject during regular intervals, such as 1 to 6 times a day, during the course of 1 or more days. Preferably, a kit contains instructions indicating the use of the dosage form for weight or appetite increase and the amount of dosage form to be taken over a specified time period.

EXAMPLES

Examples are provided below to further illustrate different features of the present invention. The examples also illustrate useful methodology for practicing the invention. These examples do not limit the claimed invention.

Example 1

MCH Receptor Sequences

Human MCH-2R amino acid and encoding cDNA sequences, and MCH-1R amino acid and encoding cDNA sequences, are as follows:

```
MCH-2R Amino Acid Sequence

MNPFHASCWNTSAELLNKSWNKEFAYQTASVVDTVILPSMIGIICSTGLVGNI      (SEQ. ID. NO. 58)

LIVFTIIRSRKKTVPDIYICNLAVADLVHIVGMPFLIHQWARGGEWVFGGPLCTI

ITSLDTCNQFACSAIMTVMSVDRYFALVQPFRLTRWRTRYKTIRINLGLWAAS

FILALPVWVYSKVIKFKDGVESCAFDLTSPDDVLWYTLYLTITTFFFPLPLILVC

YILILCYTWEMYQQNKDARCCNPSVPKQRVMKLTKMVLVLVVVFILSAAPY

HVIQLVNLQMEQPTLAFYVGYYLSICLSYASSSINPFLYILLSGNFQKRLPQIQR

RATEKEINNMGNTLKSHF

MCH-2R cDNA Sequence

ATGAATCCATTTCATGCATCTTGTTGGAACACCTCTGCCGAACTTTTAAAC       (SEQ. ID. NO. 59)

AAATCCTGGAATAAAGAGTTTGCTTATCAAACTGCCAGTGTGGTAGATAC

AGTCATCCTCCCTTCCATGATTGGGATTATCTGTTCAACAGGGCTGGTTGG

CAACATCCTCATTGTATTCACTATAATAAGATCCAGGAAAAAAACAGTCC

CTGACATCTATATCTGCAACCTGGCTGTGGCTGATTTGGTCCACATAGTTG

GAATGCCTTTTCTTATTCACCAATGGGCCCGAGGGGGAGAGTGGGTGTTT

GGGGGGCCTCTCTGCACCATCATCACATCCCTGGATACUGTAACCAATTT

GCCTGTAGTGCCATCATGACTGTAATGAGTGTGGACAGGTACTTTGCCCTC

GTCCAACCATTTCGACTGACACGTTGGAGAACAAGGTACAAGACCATCCG

GATCAATTTGGGCCTTTGGGCAGCTTCCTTTATCCTGGCATTGCCTGTCTG
```

-continued

```
GGTCTACTCGAAGGTCATCAAATTTAAAGACGGTGTTGAGAGTTGTGCTTT

TGATTTGACATCCCCTGACGATGTACTCTGGTATACACTTTATTTGACGAT

AACAACTTTTTTTTTCCCTCTACCCTTGATTTTGGTGTGCTATATTTTAATT

TTATGCTATACTTGGGAGATGTATCAACAGAATAAGGATGCCAGATGCTG

CAATCCCAGTGTACCAAAACAGAGAGTGATGAAGTTGACAAAGATGGTGC

TGGTGCTGGTGGTAGTCTTTATCCTGAGTGCTGCCCCTTATCATGTGATAC

AACTGGTGAACTTACAGATGGAACAGCCCACACTGGCCTTCTATGTGGGT

TATTACCTCTCCATCTGTCTCAGCTATGCCAGCAGCAGCATTAACCCTTTT

CTCTACATCCTGCTGAGTGGAAATTTCCAGAAACGTCTGCCTCAAATCCAA

AGAAGAGCGACTGAGAAGGAAATCAACAATATGGGAAACACTCTGAAAT

CACACTTTTAG
```

MCH-1R Amino Acid Sequence

MDLEASLLPTGPNASNTSDGPDNLTSAG-SPPRTGSISYINIIMPSVFGTICLLGIIG        (SEQ. ID. NO. 60)

NSTVIFAVVKKSKLHWCNNVPDIFIINLSVVDLLFLLGMPFMIHQLMGNGVWH

FGETMCTLITAMDANSQFTSTYILTAMAIDRYLATVHPISSTKFRKPSVATLVI

CLLWALSFISITPVWLYARLIPFPGGAVGCGIRLPNPDTDLYWFTLYQFFLAFA

LPFVVITAAYVRILQRMTSSVAPASQRSIRLRTKRVTRTAIAICLVFFVCWAPY

YVLQLTQLSISRPTLTFVYLYNAAISLGYANSCLNPFVYIVLCETFRKRLVLSV

KPAAQGQLRAVSNAQTADEERTESKGT

MCH-1R Amino Acid Sequence

```
ATGGACCTGGAAGCCTCGCTGCTGCCCACTGGTCCCAACGCCAGCAACAC        (SEQ. ID. NO. 61)

CTCTGATGGCCCCGATAACCTCACTTCGGCAGGATCACCTCCTCGCACGG

GGAGCATCTCCTACATCAACATCATCATGCCTTCGGTGTTCGGCACCATCT

GCCTCCTGGGCATCATCGGGAACTCCACGGTCATCTTCGCGGTCGTGAAG

AAGTCCAAGCTGCACTGGTGCAACAACGTCCCCGACATCTTCATCATCAA

CCTCTCGGTAGTAGATCTCCTCTTTCTCCTGGGCATGCCCTTCATGATCCA

CCAGCTCATGGGCAATGGGGTGTGGCACmGGGGAGACCATGTGCACCC

TCATGACGGCCATGGATGCCAATAGTCAGTTCACCAGCACGTACATCCTG

ACCGCCATGGCCATTGACCGCTACCTGGCCACTGTCCACCCCATCTCTTCC

ACGAAGTTCCGGAAGCCCTCTGTGGCCACCGTGGTGATCTGCCTCCTGTGG

GCCCTCTCCTTCATCAGCATCACCCCTGTGTGGCTGTATGCCAGACTCATC

CCCTTCCCAGGAGGTGCAGTGGGCTGCGGCATACGCCTGCCCAACCCAGA

CACTGACCTCTACTGGTTCACCCTGTACCAGTTTTTCCTGGCCTTTGCCCTG

CCTTTTGTGGTCATCACAGCCGCATACGTGAGGATCCTGCAGCGCATGAC

GTCCTCAGTGGCCCCCGCCTCCCAGCGCAGCATCCGGCTGCGGACAAAGA

GGGTGACCCGCACAGCCATCGCCATCTGTCTGGTCTTCTTTGTGTGCTGGG

CACCCTACTATGTGCTACAGCTGACCCAGTTGTCCATCAGCCGCCCGACCC

TCACCTTTGTCTACTTATACAATGCGGCCATCAGCTTGGGCTATGCCAACA

GCTGCCTCAACCCCTTTGTGTACATCGTGCTGTGTGAGACGTTCCGCAAAC

GCTTGGTGCTGTCGGTGAAGCGTGCAGCCCAGGGGCAGCTTCGCGCTGTC
```

-continued

```
AGCAACGCTCAGACGGCTGACGAGGAGAGGACAGAAAGCAAAGGCACCT
GA
```

Example 2

Synthesis of MCH Analogs

MCH analogs were produced using the procedures described below and varying the stepwise addition of amino acid groups. Other procedures for producing and modifying peptides are well known in the art.

Elongation of peptidyl chains on 4-(2',4'-dimethoxyphenyl-Fmoc-aminomethyl)-phenoxy resin and the acetylation of the N-terminal amino groups of the peptides was performed on a 431A ABI peptide synthesizer. Manufacture-supplied protocols were applied for coupling of the hydroxybenzotriazole esters of amino acids in N-methylpyrrolidone (NMP). The fluorenylmethyloxycarbonyl (Fmoc) group was used as a semipermanent alpha-amino protecting group, whereas the side chains protecting groups were: tert-butyl for aspartic acid and tyrosine, 2,2,4,6,7-pentamethyldihydrobenzofuran-5-sulfonyl (Pbf) for arginine, and trityl for cysteine.

Peptides were cleaved from the resin with TFA containing 5% of anisole. After 2 hours at room temperature the resin was filtered, washed with TFA and the combined filtrates were evaporated to dryness in vacuo. The residue was triturated with ether, the precipitate which formed was filtered off, washed with ether, and dried.

Crude peptides were dissolved in 5% acetic acid in water, and the pH of the solutions were adjusted to ca. 8.2 with diluted ammonium hydroxide. The reaction mixtures were stirred vigorously while 0.05% solution of potassium ferricyanide ($K_3Fe(CN)_6$) in water was added dropwise till the reaction mixture remained yellow for about 5 minutes. After an additional 20 minutes oxidation was terminated with ca. 1 ml of acetic acid and the reaction mixtures were lyophilized.

Crude lyophilized peptides were analyzed by analytical reverse-phase high-pressure liquid chromatography (RP HPLC) on a C18 Vydac column attached to a Waters 600E system with automatic Wisp 712 injector and 991 Photodiode Array detector. A standard gradient system of 0-100% buffer B in 30 minutes was used for analysis: buffer A was 0.1% trifluoroacetic acid in water and buffer B was 0.1% trifluoroacetic acid in acetonitrile. HPLC profiles were recorded at 210 nm and 280 nm. Preparative separations were performed on a Waters Delta Prep 4000 system with a semipreparative C18 RP Waters column. The above-described solvent system of water and acetonitrile, in a gradient of 20-80% buffer B in 60 minutes, was used for separation. The chromatographically homogenous compounds were analyzed by electrospray mass spectrometry.

Example 3

Aequorin Bioluminescence Functional Assay

The aequorin bioluminescence assay can be used to measure the activity of G protein-coupled receptors that couple through the $G\alpha$ protein subunit family consisting of Gq and G11. Such coupling leads to phospholipase C activation, intracellular calcium mobilization and protein kinase C activation.

Measurement of MCH receptor activity in the aequorin-expressing stable reporter cell line 293-AEQ17 (Button et al., *Cell Calcium* 14:663-671, 1993) was performed using a Luminoskan RT luminometer (Labsystems Inc., Gaithersburg, Md.). 293-AEQ17 cells ($8\times10^5$ cells plated 18 hours before transfection in a T75 flask) were transfected with 22 µg of human MCH receptor plasmid using 264 µg lipofectamine. The open reading frame cDNA (SEQ. ID. NO. 59 or SEQ. ID. NO. 61) encoding the human MCH-R2 or MCH-1R were inserted in the mammalian expression vector pcDNA-3 (Invitrogen, Carlsbad, Calif.). Following approximately 40 hours of expression the apo-aequorin in the cells was charged for 4 hours with coelenterazine (10 µM) under reducing conditions (300 µM reduced glutathione) in ECB buffer (140 mM NaCl, 20 mM KCl, 20 mM HEPES-NaOH [pH=7.4], 5 mM glucose, 1 mM $MgCl_2$, 1 mM $CaCl_2$, 0.1 mg/ml bovine serum albumin).

The cells were harvested, washed once in ECB medium and resuspended to 500,000 cells/ml. 100 µl of cell suspension (corresponding to $5\times10^4$ cells) was then injected into the test plate containing MCH or MCH analogs, and the integrated light emission was recorded over 30 seconds, in 0.5 second units. 20 µL of lysis buffer (0.1% final Triton X-100 concentration) was then injected and the integrated light emission recorded over 10 seconds, in 0.5 second units. The "fractional response" values for each well were calculated by taking the ratio of the integrated response to the initial challenge to the total integrated luminescence including the Triton X-100 lysis response.

Example 4

Radiolabeled MCH-R Binding Assay

Activity of truncated MCH analogs was assayed by measuring the ability of the analog to inhibit binding of [$^{125}$I]-human MCH (Phe$^{13}$, Tyr$^{19}$ substituted) to membranes prepared from cells stably expressing the human MCH receptor. Human MCH (Phe$^{13}$, Tyr$^{19}$ substituted) used in the assay was radiolabeled with $^{125}$I at $^{19}$Tyr to a specific activity of ~2000 Ci/mmol (NEN Life Science Products, Boston, Mass.).

Cell membranes were prepared on ice. Each T-75 flask was rinsed twice with 10 ml of Enzyme-free Cell Dissociation Buffer (Specialty Media, Lavallette, N.J.), and the cell monolayer was detached in an additional 10 ml of Enzyme-free Cell Dissociation Buffer by incubation at room temperature for 10 minutes. Dissociated cells were centrifuged (500×g for 10 minutes at 4° C.), resuspended in 5 ml homogenization buffer (10 mM Tris-HCl, pH 7.4, 0.01 mM Pefabloc, 10 µM phosphoramidon, 40 µg/ml bacitracin) and then homogenized using a glass homogenizer (10-15 strokes). The homogenate was centrifuged for 10 minutes (1,000×g at 4° C.). The resulting supernatant was then centrifuged at 38,700×g for 15 minutes at 4° C. Pelleted membranes were resuspended (passed through 25 gauge needle 5 times), snap-frozen on liquid nitrogen, and stored at −80° C. until use.

Binding was performed in a 96-well filter assay or Scintillation Proximity Assay (SPA)-based format using cell membranes from a stable CHO or HEK-293 cell line expressing the MCH receptor. For the filter assay, reactions were performed at 20° C. for 1 hour in a total volume of 0.2 ml containing: 0.05 ml of membrane suspension (~3 μg protein), 0.02 ml of [$^{125}$I]-human MCH (Phe$^{13}$, Tyr$^{19}$ substituted; 30 pM), 0.01 ml of competitor and 0.12 ml of binding buffer (50 mM Tris-HCl, pH 7.4, 10 mM MgCl$_2$, 2 mM EDTA, 200 μg/ml bacitracin, 1 μM phosphoramidon).

Bound radioligand was separated by rapid vacuum filtration (Packard Filtermate 96-well cell harvester) through GF/C filters pretreated for 1 hour with 1% polyethylenimine. After application of the membrane suspension to the filter, the filters were washed 3 times with 3 ml each of ice-cold 50 mM Tris-HCl, pH 7.4, 10 mM MgCl$_2$, 2 mM EDTA, 0.04% Tween 20 and the bound radioactivity on the filters was quantitated by scintillation counting (TopCount device). Specific binding (>80% of total) is defined as the difference between total binding and non-specific binding conducted in the presence of 100 nM unlabeled human MCH.

For the SPA-based assay, WGA-PVT beads (NEN Life Sciences Products) were resuspended in Dulbecco's PBS with calcium and magnesium (500 mg beads in 4 ml PBS). For each 96-well assay plate, 0.18 ml of beads was pre-coated with MCH receptor by mixing with 0.2 ml MCH receptor CHO cell membranes (~0.2-4 mg protein) and 1.5 ml SPA assay buffer (50 mM Tris-HCl, pH 7.4, 10 mM MgCl$_2$, 2 mM EDTA, 0.1% BSA, 12% glycerol). The suspension was mixed gently for 20 minutes, 12.3 ml of assay buffer and protease inhibitors were added (final concentration given): 2 μg/ml leupeptin, 10 μM phosphoramidon, 40 μg/ml bacitracin, 5 μg/ml aprotinin, 0.1 mM Pefabloc.

Coated beads were kept on ice until use. For each well, 0.145 ml of beads were added to Optiplate assay plates (Packard 6005190), followed by 0.002-0.004 ml of competitor and 0.05 ml of [$^{125}$I]-human MCH (Phe$^{13}$, Tyr$^{19}$ substituted; 30 pM). Binding reactions were allowed to proceed at room temperature for 3 hours. Quantitation was performed by scintillation counting (TopCount device).

Example 5

MCH Activity

The activity of different MCH analogs was measured using the procedures described in Examples 3 and 4 above. Tables 1-3 illustrate the activity of different truncated MCH analogs and mammalian MCH at MCH-1R and MCH-2R. Based on the guidance provided herein, additional MCH analogs active at the MCH-2R and MCH-1R, and selectively active at MCH-2R can be obtained.

TABLE 1

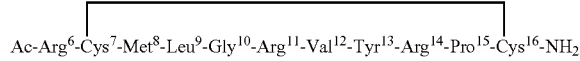

Ac-Arg$^6$-Cys$^7$-Met$^8$-Leu$^9$-Gly$^{10}$-Arg$^{11}$-Val$^{12}$-Tyr$^{13}$-Arg$^{14}$-Pro$^{15}$-Cys$^{16}$-NH$_2$

| | | MCH-1R | | | MCH-2R | | |
|---|---|---|---|---|---|---|---|
| SEQ. ID. NO. | Compound | IC$_{50}$ (nM) | EC$_{50}$ (nM) | Activation % | IC$_{50}$ (nM) | EC$_{50}$ (nM) | Activation % |
| 1 | hMCH | 0.3 | 30.9 | 100 | 0.5 | 30.7 | 100 |
| 2 | | 1.4 | 20 | 99 | 2 | 6.2 | 98 |
| 3 | ΔArg$^6$ | 1.6 | 300 | 6.5 | 38.5% @ 10 μM | 1500 | |
| 4 | Ala$^8$ | 15 | 4100 | 42 | 18 | 12 | 104 |
| 5 | Nle$^8$ | 0.5 | 44 | 105 | 0.15 | 12 | 105 |
| 6 | Sar$^{10}$ | 2.3 | 140 | 95 | 69 | 40 | 94 |
| 7 | Ala$^{10}$ | 0.59 | 31 | 104 | 4.6 | 7.7 | 97 |
| 8 | Leu$^{10}$ | 0.06 | 23 | 106 | 20 | 54 | 80 |
| 9 | Nle$^{10}$ | 0.04 | 15 | 106 | 1.8 | 16 | 103 |
| 10 | Ser$^{10}$ | 0.32 | 65 | 104 | 52 | 44 | 95 |
| 11 | Aib$^{10}$ | 90 | 1900 | 22 | 2.2 | 24 | 104 |
| 12 | Phg$^{10}$ | 2.9 | >10000 | 0.1 | 312 | 140 | 80 |
| 13 | D-Ala$^{10}$ | 490 | 1360 | 40 | 3.2 | 16 | 103 |
| 14 | D-Leu$^{10}$ | 16 | 750 | 23 | 4.1 | 36 | 83 |
| 15 | D-Nle$^{10}$ | 2.4 | 215 | 33 | 2.3 | 29 | 78 |
| 16 | D-Cha$^{10}$ | 11 | >10000 | 0.1 | 74 | 207 | 74 |
| 17 | D-Phe$^{10}$ | 18 | >10000 | 5 | 47 | 25 | 102 |
| 18 | D-Asn$^{10}$ | 97 | 3000 | 39 | 2.3 | 24 | 106 |
| 19 | D-Ser$^{10}$ | 31 | 2560 | 47 | 1.6 | 7 | 113 |
| 20 | βAla$^{10}$ | 390 | >1000 | 3.2 | 180 | 101 | 92 |
| 21 | εAbu$^{10}$ | 2.1 | 30.6 | 101 | 5 | 12.3 | 112 |
| 22 | N-Me-Arg$^{11}$ | 43 | 10 | 110 | 6.9 | 6.8 | 86 |
| 23 | Ala$^{11}$ | >1000 | >10000 | | 9.7 | >1000 | 36 |
| 24 | Harg$^{11}$ | 6.9 | 1200 | 72 | 0.4 | >10000 | 43 |
| 25 | Arg(NO$_2$)$^{11}$ | 80% @ 1 μM | >1000 | | 4.9 | >10000 | 39 |
| 26 | Nle$^{11}$ | 301 | >1000 | | 9 | 58 | 34 |
| 27 | Phe$^{13}$ | 1 | 46 | 96 | 1.5 | 12 | 94 |
| 28 | (2)Nal$^{13}$ | 0.15 | 54 | 105 | 0.8 | 19 | 90 |
| 29 | Phe(pF)$^{13}$ | 0.6 | 108 | 98 | 0.6 | 10 | 100 |
| 30 | Phe(pNH$_2$)$^{13}$ | 3.2 | 610 | 88 | 7.4 | 24 | 70 |
| 31 | Cha$^{13}$ | 0.09 | 122 | 93 | 9 | 43 | 76 |

TABLE 1-continued

Ac-Arg⁶-Cys⁷-Met⁸-Leu⁹-Gly¹⁰-Arg¹¹-Val¹²-Tyr¹³-Arg¹⁴-Pro¹⁵-Cys¹⁶-NH₂
(disulfide bond between Cys⁷ and Cys¹⁶)

| SEQ. ID. NO. | Compound | MCH-1R IC$_{50}$ (nM) | MCH-1R EC$_{50}$ (nM) | MCH-1R Activation % | MCH-2R IC$_{50}$ (nM) | MCH-2R EC$_{50}$ (nM) | MCH-2R Activation % |
|---|---|---|---|---|---|---|---|
| 32 | Sar¹⁵ | 0.36 | 25 | 113 | 21 | 12 | 91 |
| 33 | D-Cys¹⁶ | 0.8 | 133 | 76 | 2.3 | 10.5 | 90 |
| 34 | (Δ-NH₂)-Arg⁶, D-Ala¹⁰ | 30 | 2000 | 4 | 250 | 31 | 110 |
| 35 | Ala⁸, D-Ala¹⁰ | 70% @ 1 μM | >10000 | | 17 | 140 | 120 |
| 36 | D-Ala¹⁰, Harg¹¹ | 56 | >10000 | 0.1 | 0.9 | 19 | 74 |
| 37 | D-Ala¹⁰, Arg(NO₂)¹¹ | >1000 | >10000 | 0.1 | 490 | 260 | 34 |
| 38 | Ala⁸, D-Ala¹⁰, Harg¹¹ | 83% @ 10 μM | >10000 | 20 | | 730 | 49 |

IC$_{50}$ was determined using a SPA based assay.
EC$_{50}$ (nM) and % Activation at 10 μM were determined using aequorin functional assays.
"Aib" refers to isobutyric acid, "δAbu" refers to gamma-aminobutyric acid, "Phg" refers to phenylglycine, "Cha" refers to 2-cyclohexyl-alanine, "Sar" refers to sarcosine, (2')Nal refers to (2')naphthylalanine, "Harg" refers to homoarginine.

TABLE 2

X⁶-Cys⁷-Met⁸-Leu⁹-Gly¹⁰-Arg¹¹-Val¹²-Tyr¹³-Arg¹⁴-Pro¹⁵-Cys¹⁶-NH₂
(disulfide bond between Cys⁷ and Cys¹⁶)

| SEQ. ID. NO. | Position 6 modification | MCH-1R IC$_{50}$ (nM) | MCH-1R EC$_{50}$ (nM) | MCH-1R Activation % | MCH-2R IC$_{50}$ (nM) | MCH-2R EC$_{50}$ (nM) | MCH-2R Activation % |
|---|---|---|---|---|---|---|---|
| 1 | | 0.3 | 30.9 | 100 | 0.5 | 30.7 | 100 |
| 2 | | 0.5 | 20 | 99 | 2 | 6.2 | 98 |
| 39 | Arg | 0.13 | 14 | 106 | 11 | 11.6 | 109 |
| 40 | (ΔNH₂)-Arg | 0.48 | 38.5 | 49 | 15 | 7.2 | 103 |

IC$_{50}$ was determined using a SPA based assay.
EC$_{50}$ (nM) and % Activation at 10 μM were determined using aequorin functional assays.

TABLE 3

Asp¹-Phe²-Asp³-Met⁴-Leu⁵-Arg⁶-Cys⁷-Met⁸-Leu⁹-Gly¹⁰-Arg¹¹-Val¹²-Tyr¹³-Arg¹⁴-Pro¹⁵-Cys¹⁶-Trp¹⁷-Gln¹⁸-Val¹⁹
(disulfide bond between Cys⁷ and Cys¹⁶)

| SEQ. ID. NO. | Modification | MCH-1R IC$_{50}$ (nM) | MCH-1R EC$_{50}$ (nM) | MCH-1R Activation % | MCH-2R IC$_{50}$ (nM) | MCH-2R EC$_{50}$ (nM) | MCH-2R Activation % |
|---|---|---|---|---|---|---|---|
| 1 | hMCH | 0.3 | 37.2 | 100 | 0.9 | 44.7 | 100 |
| 41 | Ala¹ | 2.1 | 67.2 | 96 | 2.1 | 114.5 | 96 |
| 42 | Ala² | 0.2 | 9.9 | 97 | 1.1 | 28.6 | 102 |
| 43 | Ala³ | 0.5 | 30.2 | 97 | 1.2 | 57.2 | 95 |
| 44 | Ala⁴ | 0.5 | 12.7 | 97 | 2.4 | 38.9 | 100 |
| 45 | Ala⁵ | 0.3 | 20.3 | 96 | 2 | 17.9 | 94 |
| 46 | Ala⁶ | 4.5 | 161.2 | 81 | 200 | 852.8 | 76 |
| 47 | Ala⁸ | 40.1 | 731.4 | 56 | 40 | 125.4 | 94 |
| 48 | Ala⁹ | 0.9 | 22 | 96 | 9.5 | 95.7 | 92 |
| 49 | Ala¹¹ | 169 | 5236 | 24 | 290 | >1000 | |
| 50 | Ala¹² | 0.9 | 38.3 | 95 | 25 | 83.6 | 98 |
| 51 | Ala¹³ | 253 | 2303 | 20 | 670 | >1000 | |
| 52 | Ala¹⁴ | 1.4 | 28.3 | 97 | 62 | 186.5 | 81 |
| 53 | Ala¹⁵ | 1.9 | 34.7 | 99 | 19 | 84.2 | 96 |
| 54 | Ala¹⁷ | 0.1 | 6.8 | 100 | 5.1 | 54.2 | 95 |
| 55 | Ala¹⁸ | 0.7 | 36.1 | 99 | 9.5 | 80.8 | 97 |
| 56 | Ala¹⁹ | 0.4 | 17.4 | 100 | 8.7 | 58.9 | 99 |
| 57 | Phe¹³, Tyr¹⁷ | 0.6 | 40 | 97 | 0.07 | 1.5 | 92 |

TABLE 3-continued

Asp¹-Phe²-Asp³-Met⁴-Leu⁵-Arg⁶-[Cys⁷-Met⁸-Leu⁹-Gly¹⁰-Arg¹¹-Val¹²-Tyr¹³-Arg¹⁴-Pro¹⁵-Cys¹⁶]-Trp¹⁷-Gln¹⁸-Val¹⁹

| | | MCH-1R | | | MCH-2R | | |
|---|---|---|---|---|---|---|---|
| SEQ. ID. NO. | Modification | $IC_{50}$ (nM) | $EC_{50}$ (nM) | Activation % | $IC_{50}$ (nM) | $EC_{50}$ (nM) | Activation % |

$IC_{50}$ was determined using a SPA based assay.
$EC_{50}$ (nM) and % Activation at 10 μM were determined using aequorin functional assays.

SEQ. ID. NOs. 1 and 2 provided in Tables 1-3 refer to the human MCH sequence and a truncated form of human MCH as follows ("*" indicates cyclization (S—S)):

```
                *                                    *
Asp-Phe-Asp-Met-Leu-Arg-Cys-Met-Leu-Gly-Arg-Val-Tyr-Arg-Pro-Cys-    (SEQ. ID. NO. 1)

Trp-Gln-Val

*                           *
Ac-Arg-Cys-Met-Leu-Gly-Arg-Val-Tyr-Arg-Pro-Cys-amide                (SEQ. ID. NO. 2).
```

Other embodiments are within the following claims. While several embodiments have been shown and described, various modifications may be made without departing from the spirit and scope of the present invention.

What is claimed is:

1. An optionally substituted peptide having the structure:

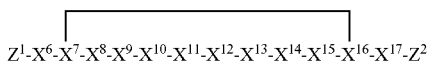

wherein $X^6$ is an optionally present amino acid that, if present, is either arginine or des-amino-arginine;
$X^7$ is cysteine;
$X^8$ is either methionine, alanine, or norleucine;
$X^9$ is either leucine or alanine;
$X^{10}$ is either glycine, alanine, leucine, norleucine, serine, sarcosine, gamma-aminobutyric acid, D-leucine, D-alanine, D-norleucine, D-asparagine, D-serine, β-alanine, phenylglycine, D-2-cyclohexyl-alanine, or D-phenylalanine;
$X^{11}$ is either arginine, alanine, N-methyl-arginine, homoarginine, citrulline, norleucine, or flitroarginine;
$X^{12}$ is valine or alanine;
$X^{13}$ is either phenylalanine, tyrosine, D-(p-benzoylpbenylalanine), (1')- and (2')-naphthylalanine, cyclohexylalanine, or mono and multi-substituted phenylalanine wherein each substituent is independently selected from the group consisting of O-alkyl, alkyl, OH, $NO_2$, $NH_2$, F, I, and Br;
$X^{14}$ is arginine;
$X^{15}$ is alanine, proline or sarcosine;
$X^{16}$ is either cysteine or D-cysteine;
$X^{17}$ is an optionally present amino acid that, if present, is either tryptophan or tyrosine,
$Z^1$ is an optionally present protecting group that, if present, is covalently joined to the N-terminal amino group;
$Z^2$ is an optionally present protecting group that, if present, is covalently joined to the C-terminal carboxy group;
or a labeled derivative of said peptide wherein said label is a detectable label selected from the group consisting of luminescent, enzymatic and radioactive;
or a pharmaceutically acceptable salt of said peptide or of said labeled derivative;
provided that one or more of the following groups are present:
$X^6$ is des-amino-arginine;
$X^{10}$ is either D-alanine, D-leucine, D-asparagine, D-norleucine, D-serine, β-alanine, phenylglycine, D-2-cyclohexyl-alanine, or D-phenylalanine, and
$X^{11}$ is nitroarginine, citrulline, norleucine, or homoarginine.

2. The peptide of claim 1, wherein one or more of the following groups are present:
$X^{10}$ is either D-alanine, D-leucine, D-asparagine, D-norleucine, D-serine, β-alanine, phenylglycine, D-2-cyclohexyl-alanine, or D-phenylalanine, and
$X^{11}$ is nitroarginine, citrulline, norleucine, or homoarginine.

3. The peptide of claim 1, wherein $X^{17}$ is not present.
4. The peptide of claim 3, wherein
$X^6$ is arginine;
$X^8$ is methionine;
$X^9$ is leucine;
$X^{12}$ is valine;
$X^{13}$ is either phenylalanine, (2')napthylalanine, p-fluorophenylalanine, or cyclohexylalanine; and
$X^{15}$ is proline or sarcosine.

5. The peptide of claim 4, wherein $X^{10}$ is either D-alanine, D-serine or D-asparagine.

6. The peptide of claim 3, wherein $X^6$ is an optionally present amino acid that, if present, is arginine, $Z^1$ is —C(O)CH$_3$ and $Z^2$ is —NH$_2$.

7. The peptide of claim 4, wherein $Z^1$ is —C(O)CH$_3$ and $Z^2$ is —NH$_2$.

8. The peptide of claim 5, wherein $Z^1$ is —C(O)CH$_3$ and $Z^2$ is —NH$_2$.

9. The peptide of claim 1, wherein said peptide is either SEQ ID 12, 13, 15, 16, 17, 18, 19, 20, 25, 26, 34, 35, or 36.

10. The peptide of claim 1, wherein said peptide is either SEQ ID NO: 13, 18, 19, 35 or 36.

11. The peptide of claim 1, wherein said peptide is SEQ ID NO: 36.

12. The peptide of claim 1, wherein said peptide is not labeled.

13. The peptide of claim 1, wherein said labeled derivative said peptide, is said peptide containing either a luminescent, enzymatic or radioactive label.

14. The peptide of claim 1, wherein a radiolabel is present.

15. The peptide of claim 4, wherein said peptide is flat labeled.

16. The peptide of claim 4, wherein said labeled derivative of said peptide, is said peptide containing either a luminescent, enzymatic or radioactive label.

17. The peptide of claim 4, wherein a radiolabel is present.

18. The peptide of claim 5, wherein said peptide is not labeled.

19. The peptide of claim 5, wherein said labeled derivative of said peptide, is said peptide containing either a luminescent, enzymatic or radioactive label.

20. The peptide of claim 5, wherein a radiolabel is present.

* * * * *

SEQUENCE LISTING

```
<160> NUMBER OF SEQ ID NOS: 61

<210> SEQ ID NO 1
<211> LENGTH: 19
<212> TYPE: PRT
<213> ORGANISM: Human
<220> FEATURE:
<221> NAME/KEY: DISULFID
<222> LOCATION: (7)...(16)

<400> SEQUENCE: 1

Asp Phe Asp Met Leu Arg Cys Met Leu Gly Arg Val Tyr Arg Pro Cys
 1               5                  10                  15

Trp Gln Val

<210> SEQ ID NO 2
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 2
```

```
Arg Cys Met Leu Gly Arg Val Tyr Arg Pro Cys
 1               5                  10

<210> SEQ ID NO 3
<211> LENGTH: 10
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (1)...(10)
<220> FEATURE:
<221> NAME/KEY: ACETYLATION
<222> LOCATION: (1)...(1)
<220> FEATURE:
<221> NAME/KEY: AMIDATION
<222> LOCATION: (10)...(10)

<400> SEQUENCE: 3

Cys Met Leu Gly Arg Val Tyr Arg Pro Cys
 1               5                  10

<210> SEQ ID NO 4
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 4

Arg Cys Ala Leu Gly Arg Val Tyr Arg Pro Cys
 1               5                  10

<210> SEQ ID NO 5
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (3)...(3)
<223> OTHER INFORMATION: Xaa = Nle

<400> SEQUENCE: 5

Arg Cys Xaa Leu Gly Arg Val Tyr Arg Pro Cys
 1               5                  10

<210> SEQ ID NO 6
<211> LENGTH: 11
<212> TYPE: PRT
<213> ORGANISM: Artificial Sequence
<220> FEATURE:
```

```
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = Sarcosine

<400> SEQUENCE: 6

Arg Cys Met Leu Xaa Arg Val Tyr Arg Pro Cys
 1               5                  10

<210> SEQ ID NO 7
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 7

Arg Cys Met Leu Ala Arg Val Tyr Arg Pro Cys
 1               5                  10

<210> SEQ ID NO 8
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 8

Arg Cys Met Leu Leu Arg Val Tyr Arg Pro Cys
 1               5                  10

<210> SEQ ID NO 9
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
```

```
<222> LOCATION: (11)...(11)
<220> FEATURE:
<221> NAME/KEY: MOD_RES
<222> LOCATION: (5)...(5)
<223> OTHER INFORMATION: Xaa = Nle

<400> SEQUENCE: 9

Arg Cys Met Leu Xaa Arg Val Tyr Arg Pro Cys
1               5                   10

<210> SEQ ID NO 10
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 10

Arg Cys Met Leu Ser Arg Val Tyr Arg Pro Cys
1               5                   10

<210> SEQ ID NO 11
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = Aib

<400> SEQUENCE: 11

Arg Cys Met Leu Xaa Arg Val Tyr Arg Pro Cys
1               5                   10

<210> SEQ ID NO 12
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = Phenylglycine
```

<400> SEQUENCE: 12

Arg Cys Met Leu Xaa Arg Val Tyr Arg Pro Cys
1               5                   10

<210> SEQ ID NO 13
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = D-alanine

<400> SEQUENCE: 13

Arg Cys Met Leu Xaa Arg Val Tyr Arg Pro Cys
1               5                   10

<210> SEQ ID NO 14
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = D-leucine

<400> SEQUENCE: 14

Arg Cys Met Leu Xaa Arg Val Tyr Arg Pro Cys
1               5                   10

<210> SEQ ID NO 15
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = D-norleucine

```
<400> SEQUENCE: 15

Arg Cys Met Leu Xaa Arg Val Tyr Arg Pro Cys
 1               5                  10

<210> SEQ ID NO 16
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = D-2-cyclohexyl-alanine

<400> SEQUENCE: 16

Arg Cys Met Leu Xaa Arg Val Tyr Arg Pro Cys
 1               5                  10

<210> SEQ ID NO 17
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = D-phenylalanine

<400> SEQUENCE: 17

Arg Cys Met Leu Xaa Arg Val Tyr Arg Pro Cys
 1               5                  10

<210> SEQ ID NO 18
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = D-asparagine

<400> SEQUENCE: 18
```

Arg Cys Met Leu Xaa Arg Val Tyr Arg Pro Cys
 1               5                   10

<210> SEQ ID NO 19
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = D-serine

<400> SEQUENCE: 19

Arg Cys Met Leu Xaa Arg Val Tyr Arg Pro Cys
 1               5                   10

<210> SEQ ID NO 20
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = bAla

<400> SEQUENCE: 20

Arg Cys Met Leu Xaa Arg Val Tyr Arg Pro Cys
 1               5                   10

<210> SEQ ID NO 21
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = Gamma-aminobutyric acid

<400> SEQUENCE: 21

Arg Cys Met Leu Xaa Arg Val Tyr Arg Pro Cys
1               5                   10

<210> SEQ ID NO 22
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (6)...(6)
<223> OTHER INFORMATION: Xaa = N-methyl-arginine

<400> SEQUENCE: 22

Arg Cys Met Leu Gly Xaa Val Tyr Arg Pro Cys
1               5                   10

<210> SEQ ID NO 23
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 23

Arg Cys Met Leu Gly Ala Val Tyr Arg Pro Cys
1               5                   10

<210> SEQ ID NO 24
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (6)...(6)
<223> OTHER INFORMATION: Xaa = Homoarginine

<400> SEQUENCE: 24

Arg Cys Met Leu Gly Xaa Val Tyr Arg Pro Cys
1               5                   10

<210> SEQ ID NO 25

```
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (6)...(6)
<223> OTHER INFORMATION: Xaa = Nitroarginine

<400> SEQUENCE: 25

Arg Cys Met Leu Gly Xaa Val Tyr Arg Pro Cys
 1               5                   10

<210> SEQ ID NO 26
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (6)...(6)
<223> OTHER INFORMATION: Xaa = Nle

<400> SEQUENCE: 26

Arg Cys Met Leu Gly Xaa Val Tyr Arg Pro Cys
 1               5                   10

<210> SEQ ID NO 27
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)

<400> SEQUENCE: 27

Arg Cys Met Leu Gly Arg Val Phe Arg Pro Cys
 1               5                   10

<210> SEQ ID NO 28
<211> LENGTH: 11
<212> TYPE: PRT
<213> ORGANISM: Artificial Sequence
<220> FEATURE:
<223> OTHER INFORMATION: MCH analog
```

```
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (8)...(8)
<223> OTHER INFORMATION: Xaa = (2')-naphthylalanine

<400> SEQUENCE: 28

Arg Cys Met Leu Gly Arg Val Xaa Arg Pro Cys
 1               5                  10

<210> SEQ ID NO 29
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (8)...(8)
<223> OTHER INFORMATION: Xaa = p-fluoro-phenylalanine

<400> SEQUENCE: 29

Arg Cys Met Leu Gly Arg Val Xaa Arg Pro Cys
 1               5                  10

<210> SEQ ID NO 30
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (8)...(8)
<223> OTHER INFORMATION: Xaa = p-amino-phenylalanine

<400> SEQUENCE: 30

Arg Cys Met Leu Gly Arg Val Xaa Arg Pro Cys
 1               5                  10

<210> SEQ ID NO 31
<211> LENGTH: 11
<212> TYPE: PRT
<213> ORGANISM: Artificial Sequence
<220> FEATURE:
<223> OTHER INFORMATION: MCH analog
<220> FEATURE:
```

```
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (8)...(8)
<223> OTHER INFORMATION: Xaa = 2-cyclohexyl-alanine

<400> SEQUENCE: 31

Arg Cys Met Leu Gly Arg Val Xaa Arg Pro Cys
 1               5                  10

<210> SEQ ID NO 32
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (10)...(10)
<223> OTHER INFORMATION: Xaa = Sarcosine

<400> SEQUENCE: 32

Arg Cys Met Leu Gly Arg Val Tyr Arg Xaa Cys
 1               5                  10

<210> SEQ ID NO 33
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (11)...(11)
<223> OTHER INFORMATION: Xaa = D-cysteine

<400> SEQUENCE: 33

Arg Cys Met Leu Gly Arg Val Tyr Arg Pro Xaa
 1               5                  10

<210> SEQ ID NO 34
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
```

```
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (1)...(1)
<223> OTHER INFORMATION: Des-amino-arginine
<220> FEATURE:
<221> NAME/KEY: MOD_RES
<222> LOCATION: (5)...(5)
<223> OTHER INFORMATION: Xaa - D-alanine

<400> SEQUENCE: 34

Xaa Cys Met Leu Xaa Arg Val Tyr Arg Pro Cys
 1               5                  10

<210> SEQ ID NO 35
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = D-alanine

SEQUENCE: 35

Arg Cys Ala Leu Xaa Arg Val Tyr Arg Pro Cys
        1               5                  10

<210> SEQ ID NO 36
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = D-alanine
<220> FEATURE:
<221> NAME/KEY: MOD_RES
<222> LOCATION: (6)...(6)
<223> OTHER INFORMATION: Xaa = Homoarginine

<400> SEQUENCE: 36

Arg Cys Met Leu Xaa Xaa Val Tyr Arg Pro Cys
 1               5                  10

<210> SEQ ID NO 37
```

```
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = D-alanine
<220> FEATURE:
<221> NAME/KEY: MOD_RES
<222> LOCATION: (6)...(6)
<223> OTHER INFORMATION: Xaa = Nitroarginine

<400> SEQUENCE: 37

Arg Cys Met Leu Xaa Xaa Val Tyr Arg Pro Cys
 1               5                  10

<210> SEQ ID NO 38
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: ACETYLATION
<222> LOCATION: (1)...(1)
<220> FEATURE:
<221> NAME/KEY: AMIDATION
<222> LOCATION: (11)...(11)
<220> FEATURE:
<221> NAME/KEY: MOD_RES
<222> LOCATION: (5)...(5)
<223> OTHER INFORMATION: Xaa = D-alanine
<220> FEATURE:
<221> NAME/KEY: MOD_RES
<222> LOCATION: (6)...(6)
<223> OTHER INFORMATION: Xaa = Homoarginine

<400> SEQUENCE: 38

Arg Cys Ala Leu Xaa Xaa Val Tyr Arg Pro Cys
 1               5                  10

<210> SEQ ID NO 39
<211> LENGTH: 10
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (2)...(11)
<220> FEATURE:
<221> NAME/KEY: AMIDATION
<222> LOCATION: (10)...(10)

<400> SEQUENCE: 39

Cys Met Leu Gly Arg Arg Tyr Arg Pro Cys
 1               5                  10

<210> SEQ ID NO 40
```

```
<211> LENGTH: 11
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (1)...(10)
<220> FEATURE:
<221> NAME/KEY: AMIDATION
<222> LOCATION: (10)...(10)

<400> SEQUENCE: 40

Arg Cys Met Leu Gly Arg Val Tyr Arg Pro Cys
1               5                   10

<210> SEQ ID NO 41
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 41

Ala Phe Asp Met Leu Arg Cys Met Leu Gly Arg Val Tyr Arg Pro Cys
1               5                   10                  15

Trp Gln Val

<210> SEQ ID NO 42
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 42

Asp Ala Asp Met Leu Arg Cys Met Leu Gly Arg Val Tyr Arg Pro Cys
1               5                   10                  15

Trp Gln Val

<210> SEQ ID NO 43
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 43

Asp Phe Ala Met Leu Arg Cys Met Leu Gly Arg Val Tyr Arg Pro Cys
1               5                   10                  15

Trp Gln Val

<210> SEQ ID NO 44
<211> LENGTH: 19
<212> TYPE: PRT
<213> ORGANISM: Artificial Sequence
<220> FEATURE:
<223> OTHER INFORMATION: MCH analog
<220> FEATURE:
```

```
<221> NAME/KEY: DISULFID
<222> LOCATION: (7)...(16)

<400> SEQUENCE: 44

Asp Phe Asp Ala Leu Arg Cys Met Leu Gly Arg Val Tyr Arg Pro Cys
 1               5                  10                  15

Trp Gln Val

<210> SEQ ID NO 45
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 45

Asp Phe Asp Met Ala Arg Cys Met Leu Gly Arg Val Tyr Arg Pro Cys
 1               5                  10                  15

Trp Gln Val

<210> SEQ ID NO 46
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 46

Asp Phe Asp Met Leu Ala Cys Met Leu Gly Arg Val Tyr Arg Pro Cys
 1               5                  10                  15

Trp Gln Val

<210> SEQ ID NO 47
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 47

Asp Phe Asp Met Leu Arg Cys Ala Leu Gly Arg Val Tyr Arg Pro Cys
 1               5                  10                  15

Trp Gln Val

<210> SEQ ID NO 48
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 48

Asp Phe Asp Met Leu Arg Cys Met Ala Gly Arg Val Tyr Arg Pro Cys
 1               5                  10                  15
```

```
<210> SEQ ID NO 49
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 49

Asp Phe Asp Met Leu Arg Cys Met Leu Gly Ala Val Tyr Arg Pro Cys
 1               5                  10                  15

Trp Gln Val

<210> SEQ ID NO 50
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 50

Asp Phe Asp Met Leu Arg Cys Met Leu Gly Arg Ala Tyr Arg Pro Cys
 1               5                  10                  15

Trp Gln Val

<210> SEQ ID NO 51
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 51

Asp Phe Asp Met Leu Arg Cys Met Leu Gly Arg Val Ala Arg Pro Cys
 1               5                  10                  15

Trp Gln Val

<210> SEQ ID NO 52
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 52

Asp Phe Asp Met Leu Arg Cys Met Leu Gly Arg Val Tyr Ala Pro Cys
 1               5                  10                  15

Trp Gln Val

<210> SEQ ID NO 53
<211> LENGTH: 19
<212> TYPE: PRT
```

```
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 53

Asp Phe Asp Met Leu Arg Cys Met Leu Gly Arg Val Tyr Arg Ala Cys
 1               5                  10                  15

Trp Gln Val

<210> SEQ ID NO 54
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 54

Asp Phe Asp Met Leu Arg Cys Met Leu Gly Arg Val Tyr Arg Pro Cys
 1               5                  10                  15

Ala Gln Val

<210> SEQ ID NO 55
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 55

Asp Phe Asp Met Leu Arg Cys Met Leu Gly Arg Val Tyr Arg Pro Cys
 1               5                  10                  15

Trp Ala Val

<210> SEQ ID NO 56
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)

<400> SEQUENCE: 56

Asp Phe Asp Met Leu Arg Cys Met Leu Gly Arg Val Tyr Arg Pro Cys
 1               5                  10                  15

Trp Gln Ala

<210> SEQ ID NO 57
<211> LENGTH: 19
<212> TYPE: PRT
<213> ORGANISM: Artificial Sequence
<220> FEATURE:
<223> OTHER INFORMATION: MCH analog
<220> FEATURE:
<221> NAME/KEY: DISULFID
<222> LOCATION: (7)...(16)
```

```
<400> SEQUENCE: 57

Asp Phe Asp Met Leu Arg Cys Met Leu Gly Arg Val Phe Arg Pro Cys
  1               5                  10                  15

Tyr Gln Val

<210> SEQ ID NO 58
<211> LENGTH: 340
<212> TYPE: PRT
<213> ORGANISM: Human

<400> SEQUENCE: 58

Met Asn Pro Phe His Ala Ser Cys Trp Asn Thr Ser Ala Glu Leu Leu
  1               5                  10                  15

Asn Lys Ser Trp Asn Lys Glu Phe Ala Tyr Gln Thr Ala Ser Val Val
             20                  25                  30

Asp Thr Val Ile Leu Pro Ser Met Ile Gly Ile Ile Cys Ser Thr Gly
         35                  40                  45

Leu Val Gly Asn Ile Leu Ile Val Phe Thr Ile Ile Arg Ser Arg Lys
     50                  55                  60

Lys Thr Val Pro Asp Ile Tyr Ile Cys Asn Leu Ala Val Ala Asp Leu
 65                  70                  75                  80

Val His Ile Val Gly Met Pro Phe Leu Ile His Gln Trp Ala Arg Gly
                 85                  90                  95

Gly Glu Trp Val Phe Gly Gly Pro Leu Cys Thr Ile Ile Thr Ser Leu
            100                 105                 110

Asp Thr Cys Asn Gln Phe Ala Cys Ser Ala Ile Met Thr Val Met Ser
        115                 120                 125

Val Asp Arg Tyr Phe Ala Leu Val Gln Pro Phe Arg Leu Thr Arg Trp
    130                 135                 140

Arg Thr Arg Tyr Lys Thr Ile Arg Ile Asn Leu Gly Leu Trp Ala Ala
145                 150                 155                 160

Ser Phe Ile Leu Ala Leu Pro Val Trp Val Tyr Ser Lys Val Ile Lys
                165                 170                 175

Phe Lys Asp Gly Val Glu Ser Cys Ala Phe Asp Leu Thr Ser Pro Asp
            180                 185                 190

Asp Val Leu Trp Tyr Thr Leu Tyr Leu Thr Ile Thr Thr Phe Phe Phe
        195                 200                 205

Pro Leu Pro Leu Ile Leu Val Cys Tyr Ile Leu Ile Leu Cys Tyr Thr
    210                 215                 220

Trp Glu Met Tyr Gln Gln Asn Lys Asp Ala Arg Cys Cys Asn Pro Ser
225                 230                 235                 240

Val Pro Lys Gln Arg Val Met Lys Leu Thr Lys Met Val Leu Val Leu
                245                 250                 255

Val Val Val Phe Ile Leu Ser Ala Ala Pro Tyr His Val Ile Gln Leu
            260                 265                 270

Val Asn Leu Gln Met Glu Gln Pro Thr Leu Ala Phe Tyr Val Gly Tyr
        275                 280                 285

Tyr Leu Ser Ile Cys Leu Ser Tyr Ala Ser Ser Ile Asn Pro Phe
    290                 295                 300

Leu Tyr Ile Leu Leu Ser Gly Asn Phe Gln Lys Arg Leu Pro Gln Ile
305                 310                 315                 320

Gln Arg Arg Ala Thr Glu Lys Glu Ile Asn Asn Met Gly Asn Thr Leu
                325                 330                 335

Lys Ser His Phe
```

<210> SEQ ID NO 59
<211> LENGTH: 1023
<212> TYPE: DNA
<213> ORGANISM: Artificial Sequence
<220> FEATURE:
<223> OTHER INFORMATION: Human MCH-2R cDNA

<400> SEQUENCE: 59

```
atgaatccat tcatgcatc ttgttggaac acctctgccg aacttttaaa caaatcctgg      60
aataaagagt ttgcttatca aactgccagt gtggtagata cagtcatcct cccttccatg    120
attgggatta tctgttcaac agggctggtt ggcaacatcc tcattgtatt cactataata    180
agatccagga aaaaaacagt ccctgacatc tatatctgca acctggctgt ggctgatttg    240
gtccacatag ttggaatgcc ttttcttatt caccaatggg cccgagggggg agagtgggtg   300
tttgggggc ctctctgcac catcatcaca tccctggata cttgtaacca atttgcctgt    360
agtgccatca tgactgtaat gagtgtggac aggtactttg ccctcgtcca accatttcga    420
ctgacacgtt ggagaacaag gtacaagacc atccggatca atttgggcct ttgggcagct    480
tcctttatcc tggcattgcc tgtctgggtc tactcgaagg tcatcaaatt taaagacggt    540
gttgagagtt gtgcttttga tttgacatcc cctgacgatg tactctggta tacactttat    600
ttgacgataa caacttttt tttccctcta cccttgattt tggtgtgcta tattttaatt    660
ttatgctata cttgggagat gtatcaacag aataaggatg ccagatgctg caatcccagt    720
gtaccaaaac agagagtgat gaagttgaca agatggtgc tggtgctggt ggtagtcttt    780
atcctgagtg ctgcccctta tcatgtgata caactggtga acttacagat ggaacagccc    840
acactggcct tctatgtggg ttattacctc tccatctgtc tcagctatgc cagcagcagc    900
attaacccctt ttctctacat cctgctgagt ggaaatttcc agaaacgtct gcctcaaatc    960
caaagaagag cgactgagaa ggaaatcaac aatatgggaa acactctgaa atcacacttt   1020
tag                                                                  1023
```

<210> SEQ ID NO 60
<211> LENGTH: 353
<212> TYPE: PRT
<213> ORGANISM: Human

<400> SEQUENCE: 60

```
Met Asp Leu Glu Ala Ser Leu Leu Pro Thr Gly Pro Asn Ala Ser Asn
  1               5                  10                  15

Thr Ser Asp Gly Pro Asp Asn Leu Thr Ser Ala Gly Ser Pro Pro Arg
             20                  25                  30

Thr Gly Ser Ile Ser Tyr Ile Asn Ile Ile Met Pro Ser Val Phe Gly
         35                  40                  45

Thr Ile Cys Leu Leu Gly Ile Ile Gly Asn Ser Thr Val Ile Phe Ala
     50                  55                  60

Val Val Lys Lys Ser Lys Leu His Trp Cys Asn Asn Val Pro Asp Ile
 65                  70                  75                  80

Phe Ile Ile Asn Leu Ser Val Val Asp Leu Leu Phe Leu Leu Gly Met
                 85                  90                  95

Pro Phe Met Ile His Gln Leu Met Gly Asn Gly Val Trp His Phe Gly
            100                 105                 110

Glu Thr Met Cys Thr Leu Ile Thr Ala Met Asp Ala Asn Ser Gln Phe
        115                 120                 125
```

-continued

```
Thr Ser Thr Tyr Ile Leu Thr Ala Met Ala Ile Asp Arg Tyr Leu Ala
    130                 135                 140
Thr Val His Pro Ile Ser Ser Thr Lys Phe Arg Lys Pro Ser Val Ala
145                 150                 155                 160
Thr Leu Val Ile Cys Leu Leu Trp Ala Leu Ser Phe Ile Ser Ile Thr
                165                 170                 175
Pro Val Trp Leu Tyr Ala Arg Leu Ile Pro Phe Pro Gly Gly Ala Val
            180                 185                 190
Gly Cys Gly Ile Arg Leu Pro Asn Pro Asp Thr Asp Leu Tyr Trp Phe
        195                 200                 205
Thr Leu Tyr Gln Phe Phe Leu Ala Phe Ala Leu Pro Phe Val Val Ile
    210                 215                 220
Thr Ala Ala Tyr Val Arg Ile Leu Gln Arg Met Thr Ser Ser Val Ala
225                 230                 235                 240
Pro Ala Ser Gln Arg Ser Ile Arg Leu Arg Thr Lys Arg Val Thr Arg
                245                 250                 255
Thr Ala Ile Ala Ile Cys Leu Val Phe Phe Val Cys Trp Ala Pro Tyr
                260                 265                 270
Tyr Val Leu Gln Leu Thr Gln Leu Ser Ile Ser Arg Pro Thr Leu Thr
            275                 280                 285
Phe Val Tyr Leu Tyr Asn Ala Ala Ile Ser Leu Gly Tyr Ala Asn Ser
        290                 295                 300
Cys Leu Asn Pro Phe Val Tyr Ile Val Leu Cys Glu Thr Phe Arg Lys
305                 310                 315                 320
Arg Leu Val Leu Ser Val Lys Pro Ala Ala Gln Gly Gln Leu Arg Ala
                325                 330                 335
Val Ser Asn Ala Gln Thr Ala Asp Glu Glu Arg Thr Glu Ser Lys Gly
            340                 345                 350
Thr
```

<210> SEQ ID NO 61
<211> LENGTH: 1062
<212> TYPE: DNA
<213> ORGANISM: Artificial Sequence
<220> FEATURE:
<223> OTHER INFORMATION: Human MCH-1R cDNA

<400> SEQUENCE: 61

```
atggacctgg aagcctcgct gctgcccact ggtcccaacg ccagcaacac ctctgatggc    60
cccgataacc tcacttcggc aggatcacct cctcgcacgg ggagcatctc ctacatcaac   120
atcatcatgc cttcggtgtt cggcaccatc tgcctcctgg gcatcatcgg gaactccacg   180
gtcatcttcg cggtcgtgaa gaagtccaag ctgcactggt gcaacaacgt ccccgacatc   240
ttcatcatca acctctcggt agtagatctc ctctttctcc tgggcatgcc cttcatgatc   300
caccagctca tgggcaatgg ggtgtggcac tttggggaga ccatgtgcac cctcatcacg   360
gccatggatg ccaatagtca gttcaccagc acctacatcc tgaccgccat ggccattgac   420
cgctacctgg ccactgtcca ccccatctct tccacgaagt tccggaagcc ctctgtggcc   480
accctggtga tctgcctcct gtgggccctc tccttcatca gcatcacccc tgtgtggctg   540
tatgccagac tcatcccctt cccaggaggt gcagtgggct gcggcatacg cctgcccaac   600
ccagacactg acctctactg gttcaccctg taccagtttt tcctggcctt tgccctgcct   660
tttgtggtca tcacagccgc atacgtgagg atcctgcagc gcatgacgtc ctcagtggcc   720
```

```
cccgcctccc agcgcagcat ccggctgcgg acaaagaggg tgacccgcac agccatcgcc    780
atctgtctgg tcttctttgt gtgctgggca ccctactatg tgctacagct gacccagttg    840
tccatcagcc gcccgaccct caccttttgtc tacttataca atgcggccat cagcttgggc    900
tatgccaaca gctgcctcaa ccccttttgtg tacatcgtgc tctgtgagac gttccgcaaa    960
cgcttggtcc tgtcggtgaa gcctgcagcc caggggcagc ttcgcgctgt cagcaacgct   1020
cagacggctg acgaggagag gacagaaagc aaaggcacct ga                     1062
```